United States Patent
De Gaulle et al.

(10) Patent No.: US 7,209,045 B2
(45) Date of Patent: Apr. 24, 2007

(54) METHOD FOR DETERMINING AND MONITORING THE AGEING OF THE BLOOD BAGS IN BLOOD TRANSFUSION UNITS AND HEALTHCARE UNITS

(75) Inventors: Antoine De Gaulle, Paris (FR); Jean-Claude Mongrenier, Saint Germain en Laye (FR)

(73) Assignee: Biolog S.A., Boulogne Billancourt (FR)

( * ) Notice: Subject to any disclaimer, the term of this patent is extended or adjusted under 35 U.S.C. 154(b) by 278 days.

(21) Appl. No.: 10/825,183

(22) Filed: Apr. 16, 2004

(65) Prior Publication Data
US 2004/0230337 A1    Nov. 18, 2004

Related U.S. Application Data

(63) Continuation of application No. PCT/FR02/03383, filed on Oct. 4, 2002.

(30) Foreign Application Priority Data

Oct. 18, 2001  (FR)  ................................ 01 13410

(51) Int. Cl.
*G08B 21/00* (2006.01)
(52) U.S. Cl. ..................... 340/603; 340/540; 340/585; 700/225; 600/368
(58) Field of Classification Search ................ 340/603, 340/572.1, 540, 585; 283/67; 422/23; 604/408; 600/368; 235/385
See application file for complete search history.

(56) References Cited

U.S. PATENT DOCUMENTS

| | | | |
|---|---|---|---|
| 4,859,360 A | * | 8/1989 | Suzuki et al. ............ 252/299.7 |
| 5,969,606 A | * | 10/1999 | Reber et al. ................ 340/540 |
| 6,113,554 A | | 9/2000 | Gilcher et al. |
| 6,285,285 B1 | | 9/2001 | Mongrenier |
| 6,402,702 B1 | | 6/2002 | Gilcher et al. |
| 2002/0013523 A1 | * | 1/2002 | Csore et al. ................ 600/368 |
| 2002/0143320 A1 | * | 10/2002 | Levin ............................ 606/1 |
| 2003/0072676 A1 | * | 4/2003 | Fletcher-Haynes et al. ... 422/23 |

FOREIGN PATENT DOCUMENTS

| | | |
|---|---|---|
| FR | 2777378 | 10/1999 |
| FR | 2796182 | 1/2001 |
| FR | 2825637 | 12/2002 |
| WO | 00/45331 | 8/2000 |

OTHER PUBLICATIONS

English Language Abstract of FR 2796182.
English Language Abstract of FR 2777378.
English Language Abstract of FR 2796182.
English Language Abstract of FR 2825637.

* cited by examiner

Primary Examiner—Jeffery Hofsass
Assistant Examiner—Hoi C. Lau
(74) Attorney, Agent, or Firm—Greenblum & Bernstein, P.L.C.

(57) ABSTRACT

Method of monitoring a blood bag, the method including monitoring a maximum allowed time dT that the blood bag may be kept outside a controlled-atmosphere enclosure and an expiration date stored in an electronic chip fixed to the blood bag. The method further including indicating whether the blood bag may be transfused to a patient when the time dT and the expiration date have not expired. The instant abstract is neither intended to define the invention disclosed in this specification nor intended to limit the scope of the invention in any way.

28 Claims, 1 Drawing Sheet

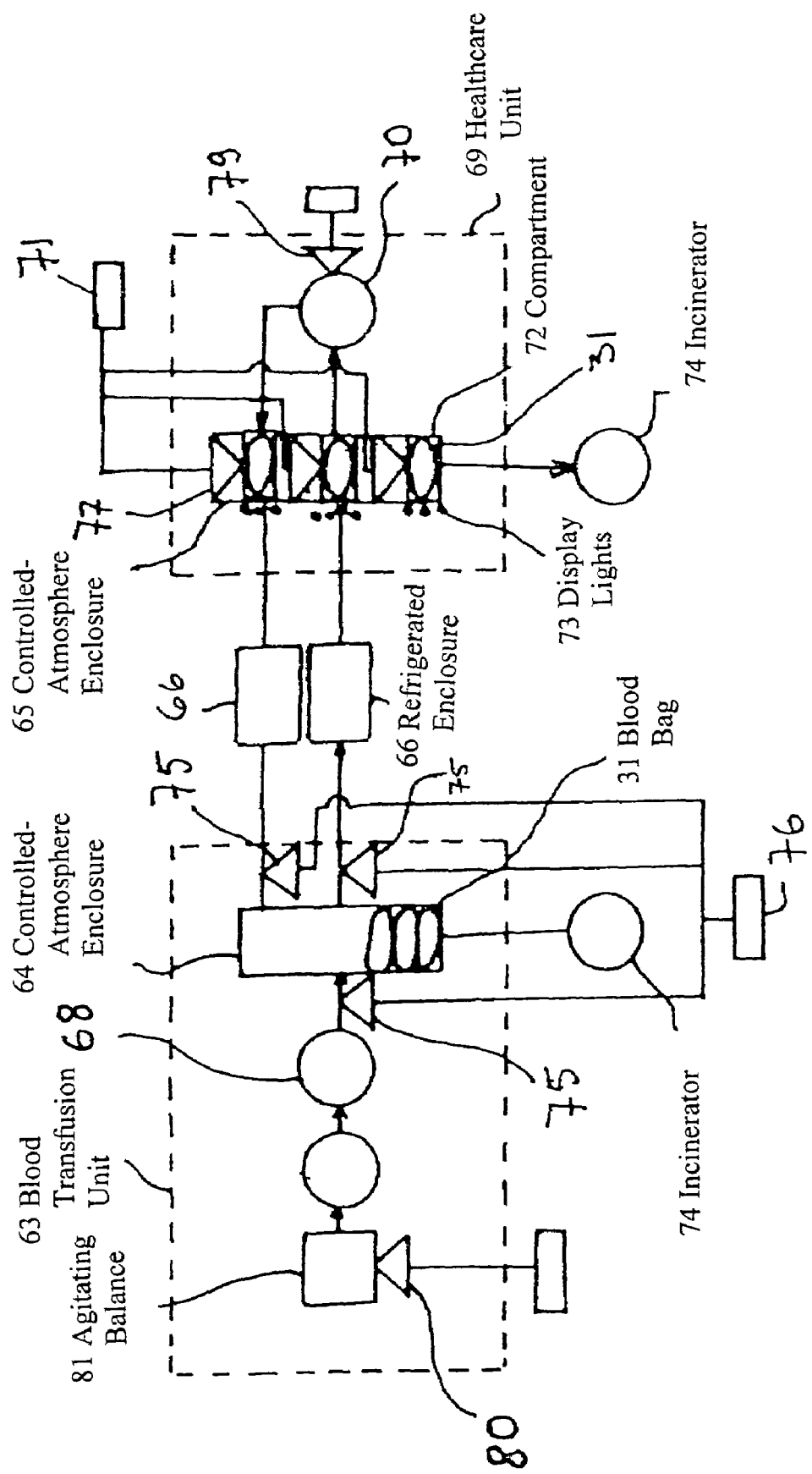

METHOD FOR DETERMINING AND MONITORING THE AGEING OF THE BLOOD BAGS IN BLOOD TRANSFUSION UNITS AND HEALTHCARE UNITS

CROSS-REFERENCE TO RELATED APPLICATIONS

The present application is a continuation of International Application No. PCT/FR02/03383 filed Oct. 4, 2002, the disclosure of which is expressly incorporated by reference herein in its entirety, and claims priority of French Application No. FR 01/13410 filed Oct. 18, 2001.

BACKGROUND OF THE INVENTION

1. Field of the Invention

The present invention relates to a method for determining and monitoring ageing of blood bags in blood transfusion units and healthcare units.

2. Discussion of Background Information

Blood bags are currently obtained from blood transfusion units and each bag is dated at the time of donation. The dating marks the start of the life of the bag and of the derived products and the life represents a useful life of the blood and lasts a predetermined time. The donated blood bags are subjected to filtering, centrifugation, and separation. The end result of which is, in particular, a derived product consisting of a bag of red blood cells which is intended to be transfused. The predetermined life of the bag of red blood cells is forty-five days starting from when the blood was donated. The bags of red blood cells are stored in the blood transfusion units and delivered as and when they are required by healthcare units. It is possible that bags of red blood cells which had been intended for dealing with an incident during an operation may not have been used. Since it is currently impossible to have a reliable guarantee of the quality of the content of the bag of red blood cells, with a view to its being used another time, it will be destroyed. Because destruction of the unused bags of red blood cells currently represents wastage of about twelve percent of all the donated blood bags, it is imperative that this should be reduced.

Since the bags of red blood cells are currently transported between the blood transfusion unit and the healthcare unit without particular precautions, a study is underway with a transportation company with a view to guaranteeing continuity of the cold chain between these two units. In this regard, the blood bag is accordingly placed in a refrigerated container, inside which there is a device indicating the temperature in the container throughout transport. By virtue of being placed in a suitable refrigerator at the healthcare unit when they arrive, the bags of red blood cells can be returned to the blood transfusion unit if they have not yet been taken out in order to be made available to a surgeon.

When blood is donated, the blood is transferred into a parent blood bag connected to a filter, which is itself connected to a primary blood bag. The primary blood bag is combined with a group of three secondary bags, to which it is connected through flexible tubes arranged in parallel. The blood from the parent blood bag is filtered and introduced into the primary blood bag. The primary blood bag is centrifuged in order to separate the red blood cells, platelets and plasma, which are then respectively transferred into each of the three bags, and it is the bag containing the red blood cells which is used to carry out blood transfusions. As a reminder, the platelets are isolated only when there is a significant need. Otherwise, they are left with the red blood cells and only two secondary bags are used.

A device for tracking blood bags according to Patent Application FR-9804802 is under development. This device assigns an electronic chip to the blood bag. Each electronic chip has a ring antenna which communicates with the ring antenna of an electronic communication device, which is connected to a computing device and is capable of supplying the electronic chip with energy and with information which it stores and which it can return to the computing device via an electronic communication device. A parent electronic chip is fixed on the parent blood bag and gathers all the information about the donor and the results of the analyses for qualifying the parent blood bag. The parent electronic chip is fixed on a flexible chip support of rectangular shape with a side length measuring a few centimeters, on which a metallized circuit is printed in loops forming the ring antenna for communication. In one aspect of the invention, the flexible chip support of the primary electronic chip is placed on one of the large faces of the parent blood bag, underneath a rectangular label covering the majority of a main face. The parent chip supports are preferably always placed at the same location with respect to the label, so as to facilitate positioning of the antenna of the electronic communication device. A Patent Application FR-9908887 describes an agitating balance provided with an electronic communication device for recording the characteristics of the blood donor and the donation conditions in the parent electronic chip of the parent blood bag. The blood from the parent blood bag is transferred into the primary blood bag by filtration. The primary blood bag has a primary electronic chip, into which the information contained in the parent electronic chip is transferred, together with the information relating to the filtration conditions. The primary blood bag is then centrifuged. The constituents are separated and are introduced into the secondary blood bags. The secondary blood bags are equipped with secondary electronic chips, which are identical to the parent and primary electronic chips and are fixed on a flexible chip support placed underneath a label covering one face of the secondary blood bag, and preferably at a location such that when the parent, primary and secondary blood bags are stacked, the parent and primary electronic chip supports do not cover one another and do not cover the secondary flexible chip supports. The secondary electronic chips of the secondary bags, that is to say the bag of red blood cells, the bag of plasma and optionally the bag of platelets, are updated by transferring information from the primary electronic chip of the primary blood bag, supplemented with information relating to the parameters used for separating the blood components. In regard to the bag of red blood cells that has been used for a blood transfusion, the secondary electronic chip which is associated with it contains the information relating to the conditions of its use and, in particular, the identity of the transfused patient.

SUMMARY OF THE INVENTION

The method to which the invention relates includes formalizing throughout its journey the status of a parent, primary or secondary blood bag, which will be referred to below as a "blood bag", equipped with an electronic chip, vis-à-vis the phenomenon of biodegradation, which will be referred to below as "ageing", so that knowledge is available at any time and in the most precise way possible as to whether the blood bag is qualified to be transfused.

One aspect of the invention includes a method for indicating whether or not a blood bag may be transfused to a patient, the blood bag having an electronic chip fixed thereto, the electronic chip having a loop antenna structured and arranged to communicate with an electronic communication device and a simplified electronic communication device having a loop antenna connected to a programmable automation device. The method including transmitting an expiration date, defined as starting from an initial time determined by donation in a parent blood bag, carried out in a blood transfusion unit, by using the electronic communication device which is combined with an agitating balance. The expiration date being stored in the electronic chip of the parent blood bag and then transferred to the electronic chip of a primary blood bag, then transferred to the electronic chips of secondary blood bags, and according to which a maximum allowed time dT for being kept outside a controlled-atmosphere enclosure is also defined. The method further including allowing the blood bag to be requalified when it is returned to the enclosure when both the time dT and the expiration date have not expired, and for the blood bag to be dequalified when one of the time dT and the expiration date have expired. Wherein when the blood bag is transported from one controlled-atmosphere enclosure to another controlled-atmosphere enclosure in a vehicle that has a refrigerated enclosure, the blood bag is requalified and a requalification date is stored in the electronic chip when a storage temperature of the refrigerated enclosure has been complied with during transport, and when the temperature has not been complied with for a time less than or equal to time dT, the blood bag is dequalified and the date is not stored when the time dT has expired. Further, wherein when the blood bag is sent to an operating theater, it is requalified at a time when taken out of a controlled-atmosphere enclosure, a requalification date then being stored in the electronic chip, and when the blood bag is not used, either the blood bag is requalified, the requalification date being stored in the electronic chip, and the blood bag is returned to the controlled-atmosphere enclosure, or it is dequalified. The method also including storing the blood bag in a compartmentalized controlled-atmosphere enclosure, each compartment being equipped with a specialized electronic communication device, the compartmentalized controlled-atmosphere enclosure being managed by a programmable automation device. The method also including checking the blood bags contained in the compartments at regular intervals for one of requalifying the blood bags, dequalifying the blood bags, and detecting that the requalified blood bag is approaching the expiration date, wherein each compartment is structured and arranged with at least three display lights which are turned on according to a result of the check. Wherein the at least three display lights indicate that the expiration date is one of sufficiently in the future, imminent, and has passed. The method also including subjecting the blood bag to a final check by an autonomous electronic communication device, wherein the check is not recorded by the electronic chip. The method further including limiting one of a number of times the blood bag may be kept outside a controlled-atmosphere enclosure and a total time for which the blood bag may be kept outside the controlled-atmosphere enclosure. Finally, the method including returning the blood bag to the blood transfusion unit when the healthcare unit has no immediate use for the blood bag, so long as a time left before reaching the expiration date is sufficient for allowing transfer to one of the blood transfusion unit and to another healthcare unit, and when the time elapsed since the last requalification is shorter than time dT.

Another aspect of the present invention includes a method of monitoring a blood bag, the method including transmitting data, including an expiration date, to a recordable medium fixed to the blood bag. The method further including monitoring a maximum allowed time dT that the blood bag may be kept outside a controlled-atmosphere enclosure and the expiration date. The method also directed to indicating whether the blood bag may be transfused to a patient when both the time dT and the expiration date have not expired, and indicating whether the blood bag may not be transfused to a patient when one of the time dT and the expiration date has expired. The method also including transporting the blood bag from one controlled-atmosphere enclosure to another controlled-atmosphere enclosure in a vehicle that has a refrigerated enclosure, and monitoring a storage temperature of the refrigerated enclosure to insure that the temperature has been maintained. The method also including storing the blood bag in a compartmentalized controlled-atmosphere enclosure, each compartment being equipped with a specialized electronic communication device, the compartmentalized controlled-atmosphere enclosure being managed by a programmable automation device. The method further includes checking the blood bags contained in the compartments at regular intervals for detecting when the blood bag is approaching the expiration date, wherein each compartment being structured and arranged with at least three display lights which are turned on according to the result of the check. The method also including subjecting the blood bag to a final check by an autonomous electronic communication device, wherein the check is not recorded by the electronic chip. The method also including limiting one of a number of times the blood bag may be kept outside a controlled-atmosphere enclosure and a total time for which the blood bag may be kept outside the controlled-atmosphere enclosure. The method is further directed to returning the blood bag to the blood transfusion unit when the healthcare unit has no immediate use for the blood bag, so long as the time left before reaching the expiration date is sufficient for allowing transfer to one of the blood transfusion unit and to another healthcare unit. The method also transferring the expiration date stored in the electronic chip of a parent blood bag to the electronic chip of a primary blood bag, and to the electronic chips of secondary blood bags.

Yet another aspect of the invention is directed to a blood bag and recordable medium electronic chip monitored according to the above-noted method. In particular, the method of monitoring a blood bag, the method including transmitting data, including an expiration date, to the recordable medium fixed to the blood bag. The method further including monitoring a maximum allowed time dT that the blood bag may be kept outside a controlled-atmosphere enclosure and the expiration date. The method also directed to indicating whether the blood bag may be transfused to a patient when both the time dT and the expiration date have not expired, and indicating whether the blood bag may not be transfused to a patient when one of the time dT and the expiration date has expired.

Another aspect of the invention includes a controlled-atmosphere enclosure used to practice a method of monitoring a blood bag, the method including transmitting data, including an expiration date, with an electronic communication device to an electronic chip that is fixed to the blood bag, the electronic chip having a loop antenna structured and arranged to communicate with the electronic communication device. The method further including monitoring a maximum allowed time dT that the blood bag may be kept outside a controlled-atmosphere enclosure and the expiration date. The method also directed to indicating whether the blood bag may be transfused to a patient when both the time dT and the expiration date have not expired, and indicating whether the blood bag may not be transfused to a patient when one of the time dT and the expiration date has expired.

Yet another aspect of the invention is directed to a vehicle having a controlled-atmosphere enclosure structured and arranged for monitoring a blood bag. The method including transmitting data, including an expiration date, to a recordable medium fixed to the blood bag. The method further including monitoring a maximum allowed time dT that the blood bag may be kept outside a controlled-atmosphere enclosure and the expiration date. The method also directed to indicating whether the blood bag may be transfused to a patient when both the time dT and the expiration date have not expired, and indicating whether the blood bag may not be transfused to a patient when one of the time dT and the expiration date has expired.

Another aspect of the invention is directed to a method of monitoring a blood bag, the method including monitoring a maximum allowed time dT that the blood bag may be kept outside a controlled-atmosphere enclosure and an expiration date stored in an electronic chip fixed to the blood bag, and indicating whether the blood bag may be transfused to a patient when the time dT and the expiration date have not expired. The method further including transporting the blood bag from one controlled-atmosphere enclosure to another controlled-atmosphere enclosure in a refrigerated enclosure, and monitoring a storage temperature of the refrigerated enclosure to insure that the temperature has been maintained. The method further including storing the blood bag in a compartmentalized controlled-atmosphere enclosure, and checking the blood bags contained in the compartments at regular intervals to detect when the blood bag is approaching the expiration date, wherein each compartment being structured and arranged with at least three display lights which are turned on according to the result of the check. The method, wherein the at least three display lights indicate that the expiration date is one of sufficiently in the future, imminent, and has passed. The method also including subjecting the blood bag to a final check by an autonomous electronic communication device, wherein the check is not recorded by the electronic chip. The method further including limiting one of a number of times the blood bag may be kept outside a controlled-atmosphere enclosure and a total time for which the blood bag may be kept outside. The method wherein each compartment being equipped with a specialized electronic communication device, the compartmentalized controlled-atmosphere enclosure being managed by a programmable automation device.

Another aspect of the invention is directed to a method for indicating whether or not the blood bag may be transfused to a patient, the blood bag having an electronic chip fixed thereto the method including defining an expiration date starting from an initial time determined by donation in a parent blood bag. The method including entering the expiration date into the electronic chip of the blood bag and defining a maximum allowed time dT the parent blood bag can be kept outside a controlled-atmosphere enclosure; and when the blood bag has been removed from the controlled-atmosphere enclosure, one of qualifying, requalifying, or dequalifying the blood bag. Requalifying includes determining when both the time dT and the expiration date have not expired, such that the blood bag is returnable to the enclosure, and dequalifying includes determining that one of the time dT and the expiration date have expired, such that the blood bag is to be destroyed. The method defining an expiration date by using the electronic communication device which is combined with an agitating balance. The method further including transferring the expiration date to the electronic chip of a primary blood bag and then transferring to the electronic chips of secondary blood bags.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted drawing by way of non-limiting examples of exemplary embodiments of the present invention, in which like reference numerals represent similar parts throughout the drawing, and wherein:

The FIGURE represents a block diagram of the steps in the method for qualifying, requalifying, and dequalifying a blood bag.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Currently, the blood transfusion unit 63 delivers a blood bag which is qualified for a period of forty-five days after the date of donation, so long as it is not removed from a controlled-atmosphere enclosure 64 under the supervision of the blood transfusion unit 63. The blood bag is taken out for immediate use in a healthcare unit 69, and it is systematically destroyed if it has not been used.

One aspect of the present invention is to permit requalification of the blood bag 31 after it has been removed from the controlled-atmosphere enclosure 64. In this regard, a maximum allowed time "dT" is defined for allowing the blood bag 31 to be kept outside a controlled-atmosphere enclosure 64, 65. Each time the blood bag 31 is outside the controlled-atmosphere enclosure 64, 65, the electronic chip is interrogated using a simplified electronic communication device 75, 77 equipped with a loop antenna. The communication device 75, 77 being connected to a programmable automation device 76, 71. If the time the blood bag 31 is kept outside the controlled-atmosphere enclosure is shorter than time dT, the blood bag is termed "requalified" so long as the period of forty-five days after the donation has not been exceeded. The period of forty-five days makes it possible to define a date which will be referred to below as the "expiration date." The expiration date is entered into the electronic chip of the parent blood bag by an electronic communication device 80 combined with an agitating balance 81. The expiration date is subsequently transferred to the primary blood bags after filtration and to the secondary blood bags after the separation phase 68. Under these conditions, when the blood bag 31 is stored in the controlled-atmosphere enclosure 64 of the blood transfusion unit 63 after the separation phase 68, the only information characterizing its ageing is the expiration date and the maximum allowed time dT for being kept outside a controlled-atmosphere enclosure 64, 65, and the date of entry into the controlled-atmosphere enclosure.

When the blood bag 31 is taken out of the controlled-atmosphere enclosure 64 and sent to a healthcare unit 69, the date of removal is compared with the expiration date of the blood bag 31 and entered into the electronic chip of the blood bag 31. The blood bag 31 is termed "qualified" if the expiration date has not been exceeded. If the expiration date has been exceeded, the blood bag 31 is deemed "dequalified" and sent for destruction. The blood bag 31 is transported to the healthcare unit 69 in a vehicle which has a refrigerated enclosure 66, and the blood bag 31 is requalified or dequalified on arrival, at the time when the blood bag 31 is transferred to the controlled-atmosphere enclosure 65 of the healthcare unit 69, on the basis of records of the temperatures of the refrigerated enclosure 66 during transport. If the transport temperature has been complied with, the blood bag is requalified and the requalification date is entered into the electronic chip of the blood bag 31. If the transport temperature has not been complied with for a time shorter than or equal to time dT, the blood bag 31 is also requalified and the requalification date is entered into the electronic chip of the blood bag 31. If the duration of time dT for noncompliance with the transport temperature has been exceeded, the bag is dequalified, the date is not entered, and the blood bag is sent for destruction. If the blood bag 31 has been requalified, the blood bag 31 is then introduced into the controlled-atmosphere enclosure 65 of the healthcare unit 69.

When the blood bag 31 is taken out of the controlled-atmosphere enclosure 65 in order to be sent to an operating theater 70, the blood bag 31 is requalified. If the blood bag 31 is not used, and it is returned to the controlled-atmosphere enclosure 65, either it is requalified and put back into the controlled-atmosphere enclosure 65 or it is dequalified. For the sake of reliability, the healthcare unit may employ a compartmentalized controlled-atmosphere enclosure 65 which is of the type previously described in Patent Application FR 0107618. The compartmentalized controlled-atmosphere enclosure 65 is managed by the programmable automation device 71 instead of being managed by a computer. Each compartment 72 being equipped with at least three display lights 73. The programmable automation device 71 inspects each compartment 72 at regular time intervals, which are much shorter than time dT. If the compartment 72 contains a blood bag 31, it checks the expiration date, the date of the last check entered into the electronic chip and the programmable automation device 71 turns on whichever of the three display lights 73 that corresponds to the result of the check. The programmable automation device 71 enters the new check date and turns on a green display light if the expiration date is sufficiently far away and the time elapsed since the last qualification or requalification is shorter than time dT. On the other hand, the programmable automation device 71 turns on an orange display light if the expiration date is imminent and the time elapsed since the last requalification is shorter than time dT. Finally, the programmable automation device 71 turns on a red display light, without entering the new check date into the electronic chip of the blood bag, in order to indicate that the bag is dequalified and should be destroyed in an incinerator 74, either because the expiration date has been exceeded or because the maximum time dT has been exceeded. When the orange display light is turned on this indicates that the blood bag ought to be sent back to the blood transfusion unit 63 if the healthcare unit has no immediate use for it, in order to avoid dequalification of the blood bag so long as the deadline left before reaching the expiration date is sufficient for allowing transfer to the blood transfusion center or to another healthcare unit.

When the blood bag is subjected to a final check by an autonomous electronic communication device 79 at the time of the transfusion, the set of controlled parameters including the time elapsed since it was taken out of the controlled atmosphere is inspected and compared with time dT. This check is not recorded in the chip as it was for the previous checks, since the transfusion date is evidence enough.

If, in the scope of normal operation, merely determining a maximum allowed time dT is sufficient to guarantee qualification of a blood bag to be transfused, drifts of the system can be avoided by limiting the number of times a blood bag may be kept outside a controlled-atmosphere enclosure, or the total time for which it may be kept outside.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for indicating whether a blood bag may be transfused to a patient, the blood bag having an electronic chip fixed thereto, the electronic chip having a loop antenna structured and arranged to communicate with an electronic communication device and a simplified electronic communication device having a loop antenna connected to a programmable automation device, the method comprising:

transmitting an expiration date, defined as starting from an initial time determined by donation in a parent blood bag, carried out in a blood transfusion unit, by using the electronic communication device which is combined with an agitating balance, the expiration date being stored in the electronic chip of the parent blood bag and then transferred to the electronic chip of a primary blood bag, then transferred to the electronic chips of secondary blood bags; defining a maximum allowed time dT for being kept outside a controlled-atmosphere enclosure; and allowing the blood bag to be requalified when it is returned to the enclosure when both the time dT and the expiration date have not expired, and for the blood bag to be dequalified when one of the time dT and the expiration date have expired.

2. The method according to claim 1, wherein when the blood bag is transported from one controlled-atmosphere enclosure to another controlled-atmosphere enclosure in a vehicle that has a refrigerated enclosure, the blood bag is requalified and a requalification date is stored in the electronic chip when a storage temperature of the refrigerated enclosure has been complied with during transport, and when the temperature has not been complied with for a time less than or equal to time dT, the blood bag is dequalified and the date is not stored when the time dT has expired.

3. The method according to claim 1, wherein when the blood bag is sent to an operating theater, it is requalified at a time when taken out of a controlled-atmosphere enclosure, a requalification date then being stored in the electronic chip, and when the blood bag is not used, either the blood bag is requalified, the requalification date being stored in the electronic chip, and the blood bag is returned to the controlled-atmosphere enclosure, or it is dequalified.

4. The method according to claim 1, further comprising:
storing the blood bag in a compartmentalized controlled-atmosphere enclosure, each compartment being equipped with a specialized electronic communication device, the compartmentalized controlled-atmosphere enclosure being managed by a programmable automation device;
checking the blood bags contained in the compartments at regular intervals for one of requalifying the blood bags, dequalifying the blood bags, and detecting that the requalified blood bag is approaching the expiration date,
wherein each compartment is structured and arranged with at least three display lights which are turned on according to a result of the check.

5. The method according to claim 4, wherein the at least three display lights indicate that the expiration date is one of sufficiently in the future, imminent, and has passed.

6. The method according to claim 1, further comprising:
subjecting the blood bag to a final check by an autonomous electronic communication device,
wherein the check is not recorded by the electronic chip.

7. The method according to claim 1, further comprising:
limiting one of a number of times the blood bag may be kept outside a controlled-atmosphere enclosure and a total time for which the blood bag may be kept outside the controlled-atmosphere enclosure.

8. The method according to claim 1, further comprising:
returning the blood bag to the blood transfusion unit when the healthcare unit has no immediate use for the blood bag, so long as a time left before reaching the expiration date is sufficient for allowing transfer to one of the blood transfusion unit and to another healthcare unit, and when the time elapsed since the last requalification is shorter than time dT.

9. A method of monitoring a blood bag, the method comprising:
transmitting data, including an expiration date, to a recordable medium fixed to the blood bag;
monitoring a maximum allowed time dT that the blood bag may be kept outside a controlled-atmosphere enclosure and the expiration date;
indicating whether the blood bag may be transfused to a patient when both the time dT and the expiration date have not expired; and
indicating whether the blood bag may not be transfused to a patient when one of the time dT and the expiration date has expired.

10. The method according to claim 9, further comprising:
transporting the blood bag from one controlled-atmosphere enclosure to another controlled-atmosphere enclosure in a vehicle that has a refrigerated enclosure; and
monitoring a storage temperature of the refrigerated enclosure to insure that the temperature has been maintained.

11. The method according to claim 9, further comprising:
storing the blood bag in a compartmentalized controlled-atmosphere enclosure, each compartment being equipped with a specialized electronic communication device, the compartmentalized controlled-atmosphere enclosure being managed by a programmable automation device;
checking the blood bags contained in the compartments at regular intervals for detecting when the blood bag is approaching the expiration date,
wherein each compartment being structured and arranged with at least three display lights which are turned on according to the result of the check.

12. The method according to claim 9, further comprising:
subjecting the blood bag to a final check by an autonomous electronic communication device,
wherein the check is not recorded by the electronic chip.

13. The method according to claim 9, further comprising:
limiting one of a number of times the blood bag may be kept outside a controlled-atmosphere enclosure and a total time for which the blood bag may be kept outside the controlled-atmosphere enclosure.

14. The method according to claim 9, further comprising:
returning the blood bag to the blood transfusion unit when the healthcare unit has no immediate use for the blood bag, so long as the time left before reaching the expiration date is sufficient for allowing transfer to one of the blood transfusion unit and to another healthcare unit.

15. The method according to claim 9, further comprising:
transferring the expiration date stored in the electronic chip of a parent blood bag to the electronic chip of a primary blood bag, and to the electronic chips of secondary blood bags.

16. A blood bag and recordable medium monitored in accordance with the method of claim 9.

17. A controlled-atmosphere enclosure structured and arranged to practice the method of claim 9.

18. A vehicle having a controlled-atmosphere enclosure structured and arranged to practice the method of claim 9.

19. A method of monitoring a blood bag, the method comprising:
monitoring a maximum allowed time dT that the blood bag may be kept outside a controlled-atmosphere enclosure and an expiration date stored in an electronic chip fixed to the blood bag; and
indicating whether the blood bag may be transfused to a patient when the time dT and the expiration date have not expired.

20. The method according to claim 19, further comprising:
transporting the blood bag from one controlled-atmosphere enclosure to another controlled-atmosphere enclosure in a refrigerated enclosure; and
monitoring a storage temperature of the refrigerated enclosure to insure that the temperature has been maintained.

21. The method according to claim 19, further comprising:
storing the blood bag in a compartmentalized controlled-atmosphere enclosure; and
checking the blood bags contained in the compartments at regular intervals to detect when the blood bag is approaching the expiration date, wherein each compartment being structured and arranged with at least three display lights which are turned on according to the result of the check.

22. The method according to claim 21, wherein the at least three display lights indicate that the expiration date is one of sufficiently in the future, imminent, and has passed.

23. The method according to claim 19, further comprising:
subjecting the blood bag to a final check by an autonomous electronic communication device,
wherein the check is not recorded by the electronic chip.

24. The method according to claim 19, further comprising:
limiting one of a number of times the blood bag may be kept outside a controlled-atmosphere enclosure and a total time for which the blood bag may be kept outside.

25. The method according to claim 19, wherein each compartment being equipped with a specialized electronic communication device, the compartmentalized controlled-atmosphere enclosure being managed by a programmable automation device.

26. A method for indicating whether the blood bag may be transfused to a patient, the blood bag having an electronic chip fixed thereto the method comprising:
defining an expiration date starting from an initial time determined by donation in a parent blood bag;
entering the expiration date into the electronic chip of the blood bag and defining a maximum allowed time dT the parent blood bag can be kept outside a controlled-atmosphere enclosure; and
when the blood bag has been removed from the controlled-atmosphere enclosure, one of qualifying, requalifying, or disqualifying the blood bag, wherein requalifying comprises determining when both the time dT and the expiration date have not expired, whereby the blood bag is returnable to the enclosure, and wherein dequalifying comprises determining that one of the time dT and the expiration date have expired, whereby the blood bag is to be destroyed.

27. The method according to claim 26, wherein the defining an expiration date is carried out in a blood transfusion unit, by using the electronic communication device which is combined with an agitating balance.

28. The method according to claim 26, further comprising:
transferring the expiration date to the electronic chip of a primary blood bag and then transferring to the electronic chips of secondary blood bags.

* * * * *